(12) United States Patent
Casty et al.

(10) Patent No.: US 7,148,392 B2
(45) Date of Patent: Dec. 12, 2006

(54) SEPARATION OF 1-BUTENE FROM $C_4$ FEED STREAMS

(75) Inventors: Gary L. Casty, League City, TX (US); Richard B. Hall, Whitehouse Station, NJ (US); Sebastian C. Reyes, Branchburg, NJ (US); Robert P. Reynolds, Jr., Clinton, NJ (US); Karl G. Strohmaier, Port Murray, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 507 days.

(21) Appl. No.: 10/464,584

(22) Filed: Jun. 17, 2003

(65) Prior Publication Data

US 2004/0260138 A1 Dec. 23, 2004

(51) Int. Cl.
*C07C 7/12* (2006.01)
(52) U.S. Cl. .................. 585/820; 585/822; 585/825; 585/826; 585/829; 95/144
(58) Field of Classification Search .................. 95/144; 585/820, 822, 825, 826, 829
See application file for complete search history.

(56) References Cited

U.S. PATENT DOCUMENTS

| | | | |
|---|---|---|---|
| 2,850,549 A | 9/1958 | Ray | 260/677 |
| 2,889,893 A | 6/1959 | Glenham et al. | 183/114.2 |
| 2,894,998 A | 7/1959 | Glenham et al. | 585/631 |
| 3,061,654 A | 10/1962 | Eensheimer et al. | 585/820 |
| 3,078,636 A | 2/1963 | Milton | 95/144 |
| 3,078,644 A | 2/1963 | Milton | 95/144 |
| 3,094,569 A | 6/1963 | Thomas | 95/117 |
| 3,151,178 A | 9/1964 | Etherington | 585/829 |
| 3,176,455 A | 4/1965 | Collins et al. | 95/104 |
| 3,524,895 A | 8/1970 | Chen et al. | 585/820 |
| 3,531,539 A | 9/1970 | Tidwell | 585/251 |
| 3,600,453 A * | 8/1971 | Reichenbacher et al. | 585/825 |
| 3,723,561 A | 3/1973 | Priegnitz | 585/820 |
| 3,763,261 A | 10/1973 | Sobel | 585/332 |
| 4,186,082 A | 1/1980 | Lin et al. | 208/310 Z |

(Continued)

FOREIGN PATENT DOCUMENTS

| | | |
|---|---|---|
| EP | 0572239 B1 | 10/1996 |
| EP | 0943595 B1 | 1/2002 |

OTHER PUBLICATIONS

Richter M., et al.; "Molecular Sieving of N-Butenes by Zeolite Erionite and by Isostructural Silicoaluminophosphate SAPO-17", *Studies in Surface Science and Catalysis*, Elsevier Science B.V., Amsterdam, NL, vol. 84, 1994, pp. 1285-1292.

(Continued)

*Primary Examiner*—Glenn Caldarola
*Assistant Examiner*—Prem C. Singh
(74) *Attorney, Agent, or Firm*—Paul E. Purwin; Robert A. Migliorini

(57) ABSTRACT

In a process for selectively separating 1-butene from a $C_4$ feed stream comprising at least 1-butene, cis-2-butene and trans-2-butene, the feed stream is passed through a first bed of an adsorbent comprising a crystalline microporous material to form a substantially trans-2-butene-free effluent stream. Then, the substantially trans-2-butene-free effluent stream is passed through a second bed of an adsorbent comprising a crystalline microporous material to form a substantially 1-butene-free effluent stream, whereby the 1-butene is separated from the feed stream. The adsorbed 1-butene is then typically desorbed from the second adsorbent bed either by lowering the pressure or raising the temperature of the bed.

17 Claims, 8 Drawing Sheets

U.S. PATENT DOCUMENTS

| | | | |
|---|---|---|---|
| 4,194,892 A | 3/1980 | Jones et al. | 95/95 |
| 4,310,440 A | 1/1982 | Wilson et al. | 502/208 |
| 4,433,195 A | 2/1984 | Kulprathipanja | 585/820 |
| 4,455,445 A | 6/1984 | Neuzil et al. | 585/820 |
| 4,769,047 A | 9/1988 | Dye | 95/97 |
| 4,804,802 A | 2/1989 | Evans et al. | 585/734 |
| 4,861,739 A | 8/1989 | Pellet et al. | 502/64 |
| 4,917,711 A | 4/1990 | Xie et al. | 95/106 |
| 5,220,102 A | 6/1993 | Funk et al. | 585/829 |
| 5,245,099 A | 9/1993 | Mitariten | 585/650 |
| 5,276,246 A | 1/1994 | McCulloch et al. | 585/829 |
| 5,292,990 A | 3/1994 | Kantner et al. | 585/820 |
| 5,365,011 A | 11/1994 | Ramachandran et al. | 585/829 |
| 5,888,921 A | 3/1999 | Tsang et al. | 502/64 |
| 6,022,398 A | 2/2000 | Cho et al. | 95/98 |
| 6,200,366 B1 | 3/2001 | Bulow et al. | 95/101 |
| 6,225,518 B1 | 5/2001 | Sohn et al. | 585/826 |
| 6,284,021 B1 | 9/2001 | Lu et al. | 95/96 |
| 6,293,999 B1 | 9/2001 | Cheng et al. | 95/96 |
| 6,296,688 B1 | 10/2001 | Cheng et al. | 95/101 |
| 6,488,741 B1 * | 12/2002 | Olson | 95/144 |

OTHER PUBLICATIONS

Richter M., et al.; "Molecular Sieving of N-Butenes by Microporous Silicoaluminophosphates", *J. Chem. Soc., Chem. Commun.*, 1993, pp. 1616-1617.

Kondo J., et al.; Migration of butene isomers onto the acid OH groups in small micropores of ferrierite, *Catalysis Today*, vol. 63, 2000, pp. 305-308.

Zhu W., et al.; "Selective adsorption of unsaturated linear $C_4$ molecules on the all-silica DD3R", *Phys. Chem. Chem. Phys.*, 2000, 2, pp. 1773-1779.

Zhu W., et al.; Shape selectivity in the adsorption of propane/propene on the all-silica DD3R:, *Chem. Commun.*, 1999, pp. 2453-2454.

* cited by examiner

SEPARATION OF 1-BUTENE FROM C$_4$ FEED STREAMS

FIELD OF THE INVENTION

This invention relates to a process for separating 1-butene from mixtures of low molecular weight hydrocarbons. In particular, the present invention is for an adsorption-based method to separate 1-butene from a C$_4$ feed stream using microporous crystalline materials.

BACKGROUND OF THE INVENTION

The separation of 1-butene from low molecular weight hydrocarbon mixtures is an important operation in the chemical and petrochemical industries. Catalytic cracking and steam cracking are among the most common and large scale processes leading to these mixed hydrocarbon streams. In the production of methanol to olefins, mixed butene streams are also produced in significant amounts as by-products. These butene streams are typically comprised of both structural and olefin isomers. The need to recover 1-butene from these streams, in particular, is one of high economic significance in providing clean feeds for subsequent processes, such as polymerizations where 1-butene is an important co-monomer in the reactions. However, despite the close proximity in boiling points between 1-butene, trans-2-butene and cis-2-butene, these components are presently separated through a combination of catalytic and super fractionation distillation. The large size of the columns and the energy intensity of such distillation processes have, however, created large incentives for alternative means of effecting these separations in a more energy-efficient and cost-effective manner.

Some of the leading alternatives to distillation involve the use of adsorbents that exploit their ability to selectively adsorb some of the components from the mixture. This has given rise to various forms of pressure and temperature swing adsorption (PSA/TSA) processes in which the mixture is first contacted with an adsorbent material under conditions where one or more of the components are selectively removed. The loaded material is then typically exposed to a lower pressure and/or higher temperature environment where the adsorbed components are released and recovered at a higher purity level. Economic viability requires adsorbent materials that can deliver high separation selectivity, high adsorption capacity, and short duration cycles. An additional and critically important requirement is that the material should not catalyze chemical reactions that might lower the recovery of the desired components and/or render the adsorbent inactive.

Among the adsorbents which have been proposed for the recovery of olefins from hydrocarbon mixtures are ion exchange resins, mesoporous solids, activated carbons, and zeolites. Ion exchange resins and mesoporous solids usually exploit equilibrium adsorption properties in which some of the components are preferentially adsorbed over suitably dispersed chemical agents. They principally rely on the adsorption affinity of cationic active centers such as Ag and Cu ions for the double bond in the olefins (e.g., propylene). The characteristic time associated with the adsorption cycle is that required to bring the mixture close to thermodynamic equilibrium with the adsorbent. Since these materials rely on adsorption equilibrium properties, the diffusion rates of the various components within the adsorbent do not influence the selectivity of the separation process. Rapid diffusion of the species into the adsorbent material is, however, highly desirable in order to speed up the contacting of the species with the adsorption sites and thus lead to adsorption/desorption cycles that have a short duration. Activated carbons and zeolites, on the other hand, typically resort to a combination of adsorption affinity and diffusion control. The diffusional effects in these cases, which are exploited advantageously, are usually a consequence of the small pores that make up these high surface area carbons and zeolites. Two related cases of diffusion control are of interest here. In one extreme case, the separation is achieved by totally excluding the diffusion of some of the components into the adsorbent. The second case exploits a sufficiently large difference in diffusion rates to allow the preferential uptake of some of the components within a predetermined adsorption time. This is typically referred to as a kinetic-based separation scheme. Thus, carbons are usually activated to very high surface area forms in order to provide textural properties and pore sizes that maximize the number of adsorption sites per unit mass of the material while selectively controlling diffusional transport into the structure. In many applications, aluminosilicate and silicate zeolites have become even more attractive than activated carbons because of the ever increasing possibilities afforded by new synthetic routes, which allow for a more flexible and precise control of chemical composition, pore size, and pore volume. The tetrahedrally coordinated atoms in these microporous materials form ring structures of precise dimensions that selectively control the diffusional access to the internal pore volume.

Eight-membered ring zeolites, in particular, have been actively investigated for the separation of small molecular weight hydrocarbons because they possess window sizes that are comparable to molecular dimensions and because they can provide high adsorption capacities. A typical example is the Linde type A zeolite which is characterized by a set of three-dimensional interconnected channels having 8-membered ring window apertures. The effective size of the windows can be controlled by appropriately selecting the type of charge-balancing cations. This has given rise to the potassium (3A), sodium (4A), and calcium (5A) forms, which have nominal window sizes of about 3 Å, 3.8 Å, and 4.3 Å, respectively. Thus, for example, EP-B-572239 discloses a PSA process for separating an alkene, such as propylene, from a mixture comprising said alkene and one or more alkanes by passing the mixture through at least one bed of zeolite 4A at a temperature above 323° K to preferentially adsorb said alkene and then desorbing the alkene from the bed. EP-A-943595 describes a similar process in which the zeolite adsorbent is zeolite A having, as its exchangeable cations, about 50% to about 85% of sodium ions, about 15% to about 40% of potassium ions and 0% to about 10% of other ions selected from Group IA ions (other than sodium and potassium), Group IB ions, Group IIA ions, Group IIIA ions, Group IIIB ions and lanthanide ions.

In applications involving zeolites, it is well known that the control of window size is critically important for achieving high separation selectivities. For a given zeolite structure type, the effective size of the windows can sometimes be modified by partially blocking or unblocking the windows with pre-selected charge-balancing cations. This provides a reasonable, but not necessarily optimal, control of window size because of the inherent difficulties of precisely placing these cations in a uniform manner throughout the structure. More importantly, the propensity of these cations to promote or participate in undesired reactions can lead to detrimental isomerization, oligomerization, and polymerization reactions of olefins. These reactions not only lower the recovery of the desired components, they are also likely to render the adsorbent inactive. The double bonds in the olefins are particularly prone to attack even by mildly acidic sites and this may severely limit the temperature and partial pressures at which the separation process can be carried out. This issue of chemical reactivity is illustrated, for example, by the work of M. Richter, et al., "Sieving of n-Butenes by Microporous Silicoaluminophosphates," J. Chem. Soc. Chem. Commun. 21, 1616–17 (1993), where a proposal is made for the use of SAPO-17 (ERI) for separating trans-2-butene from 1-butene and cis-2-butene. They report that SAPO-17 exhibits detrimental catalytic activity even at mild temperatures (395° K). Their work also shows that at 333° K the amount of trans-2-butene adsorbed on SAPO-17 exceeds that of the other isomers by a factor of approximately 7. A separation selectivity factor of 7 does not appear to be sufficient for a selective separation process in which trans-2-butene can be produced in high purity and, more importantly, the key component, 1-butene, is not separated from cis-2-butene.

In an effort to control chemical reactivity more reliably, there is a growing interest in the use of non-acidic, all-silica zeolites. Since these siliceous zeolites require no extra-framework balancing cations, the size of the windows is much more uniform throughout the crystals and largely determined by the crystal structure. Thus, for example, the potential of DDR for separating propane and propylene has been recently reported. See W. Zhu, et al., "Shape Selectivity in the Adsorption of Propane/Propene on the All-Silica DD3R," *Chem. Commun.*, 2453–54 (1999). This crystalline microporous silicate has a two-dimensional pore system formed by 8-membered rings of tetrahedrally coordinated atoms with a nominal window size of 3.6Å×4.4Å (see Atlas of Zeolites Framework Types, Fifth Revised Edition, pages 108–109, 2001). Diffusion and adsorption measurements on this material indicate that only propylene is able to access the interior of the crystallites. The exclusion of propane from the adsorbent interior was suggested as the basis for a very selective separation scheme. The size of the DDR windows, however, appears to be so close to the effective kinetic diameter of propylene that the diffusion rates are very low and this could lead to undesirably long adsorption and desorption cycles. Similar arguments may limit the use of DDR for separating the linear butene isomers. The use of DDR for this purpose is discussed by W. Zhu, et al., "Selective adsorption of unsaturated linear $C_4$ molecules on the all-silica DD3R," Phys. Chem. Chem. Phys. 2, 1773–1779 (2002). Their experiments indicate that only trans-2-butene is able to diffuse into the structure, while 1-butene and cis-2-butene are excluded. The key component, 1-butene, is not recovered as a pure component and the duration of the associated adsorption/desorption cycles for recovering trans-2-butene are likely long due to its low rate of diffusion into the material.

The advantages of reactivity control and size exclusion afforded by materials like DDR may not optimally meet all the necessary requirements for an efficient separation process. The window size also has to be optimally controlled such that short duration cycles are achieved.

SUMMARY OF THE INVENTION

According to the invention there is provided a process for separating 1-butene from a $C_4$ feed stream comprising at least 1-butene, trans-2-butene and cis-2-butene. The novel process comprises passing the feed stream through a first bed of an adsorbent comprising a crystalline microporous material to form a substantially trans-2-butene-free effluent stream. The effluent stream is then passed through a second bed of an adsorbent comprising a crystalline microporous material to form a substantially 1-butene-free effluent stream. Typically, the 1-butene is recovered by desorbing the 1-butene from the second adsorbent bed.

Preferably, the crystalline microporous materials are non-acidic and have at least one system of channels, wherein each system is defined by an 8-membered ring of tetrahedrally coordinated framework T-atoms. More preferably, the crystalline microporous materials have a system of three interconnecting 8-membered ring channels. The preferred framework T-atoms for the first adsorbent bed are made of silicon and derivatives thereof, and for the second adsorbent bed are made of phosphorus and derivatives thereof.

Preferably, the porous crystalline material of the first adsorbent bed is selected from either Si-CHA or ITE.

Preferably, the porous crystalline material of the second adsorbent bed is either aluminophosphates, gallophosphates, galloaluminophosphates, metalloaluminophosphates or metalloaluminophosphosilicates. Most preferably, the porous crystalline material of the second adsorbent bed is selected from AlPO-34, GaPO-34, AlPO-18 or GaPO-18.

DETAILED DESCRIPTION OF THE INVENTION

Figure 1:
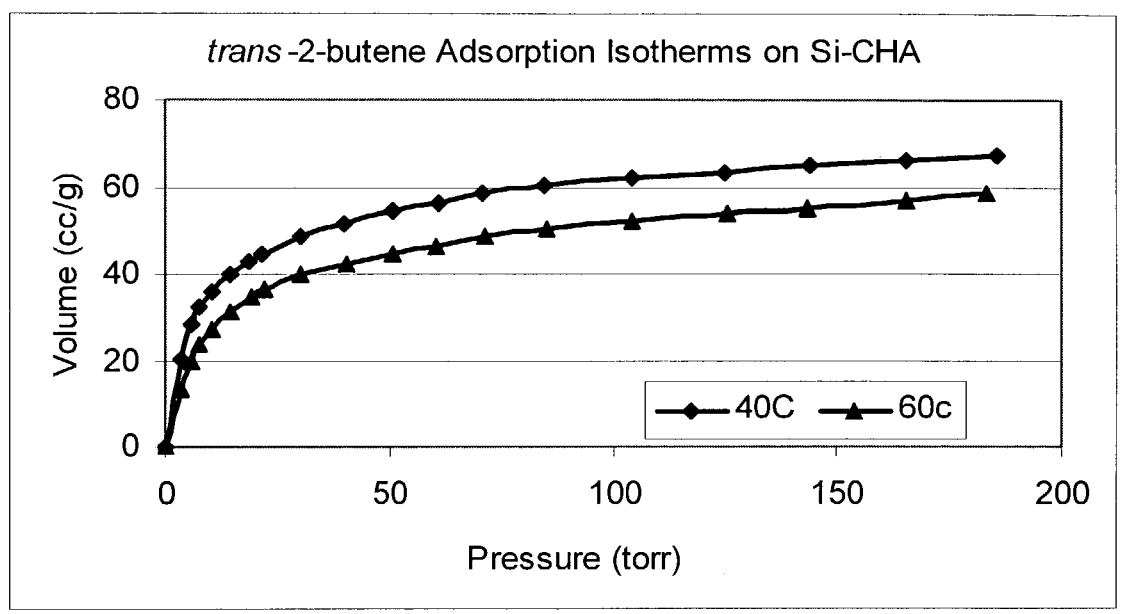
FIG. 1 shows the adsorption isotherm data for trans-2-butene on Si-CHA at 40° C. and 60° C.
Figure 2:
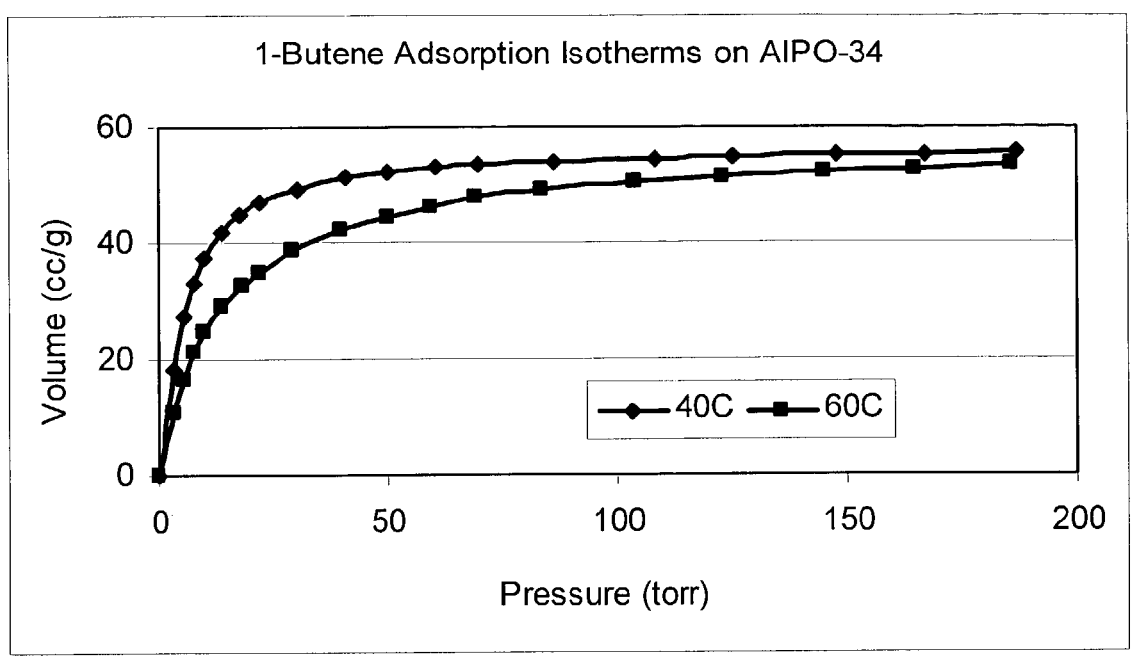
FIG. 2 shows the adsorption isotherm data for 1-butene on AlPO-34 at 40° C. and 60° C.
Figure 3:
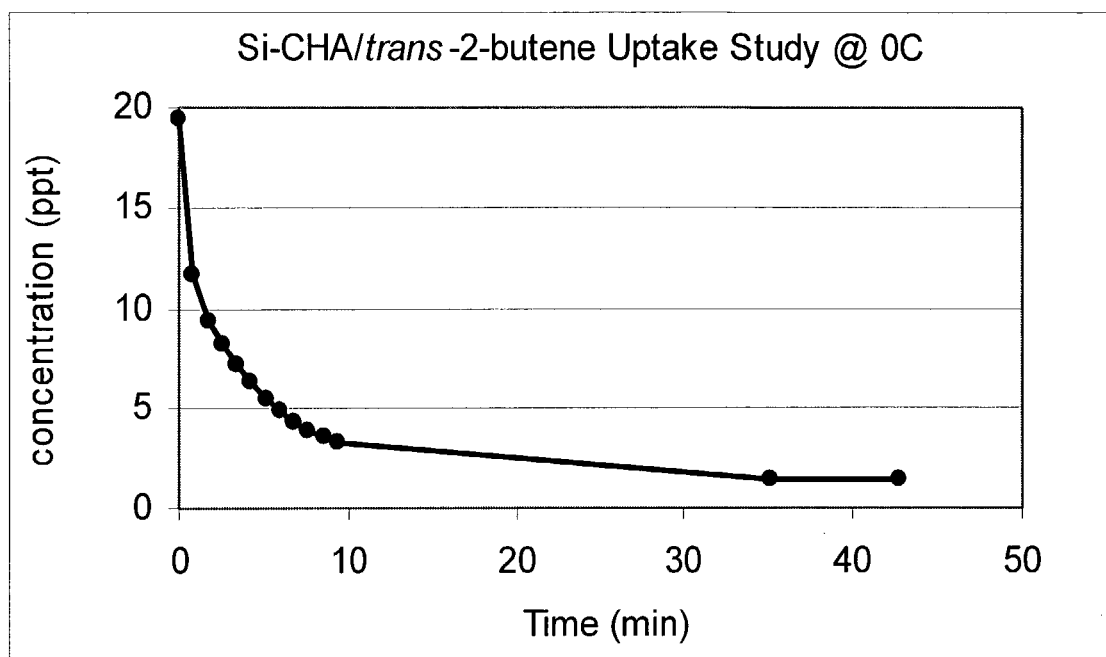
FIGS. 3–4 show the adsorption uptake data for trans-2-butene (at 0° C.) and 1-butene (at 40° C.), respectively, using Si-CHA.
Figure 4:
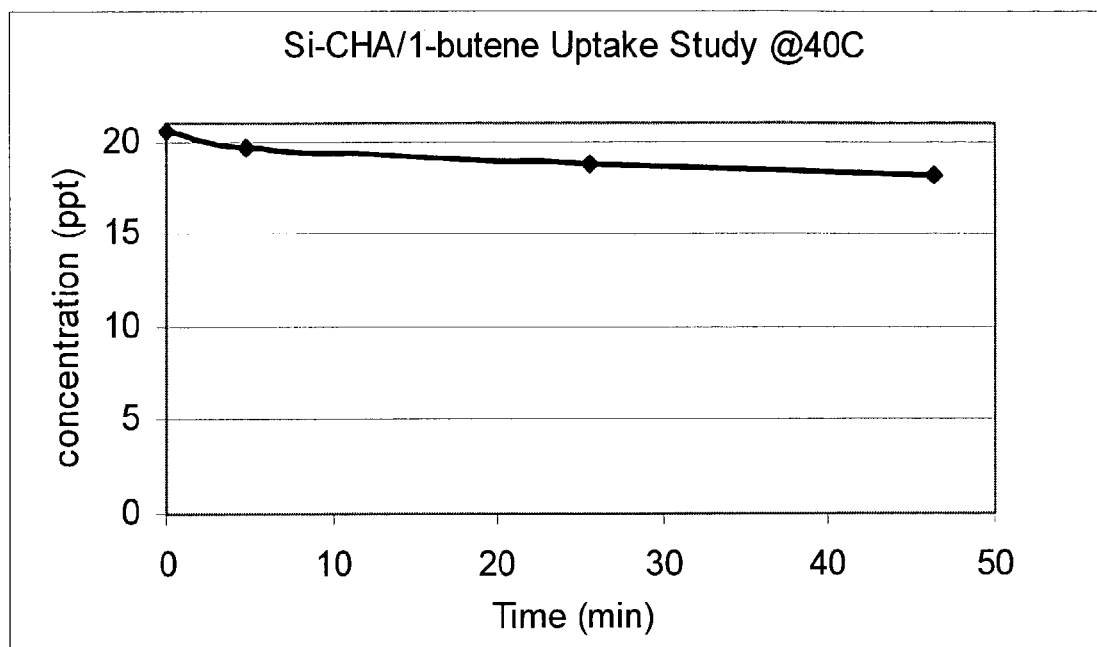
Figure 5:
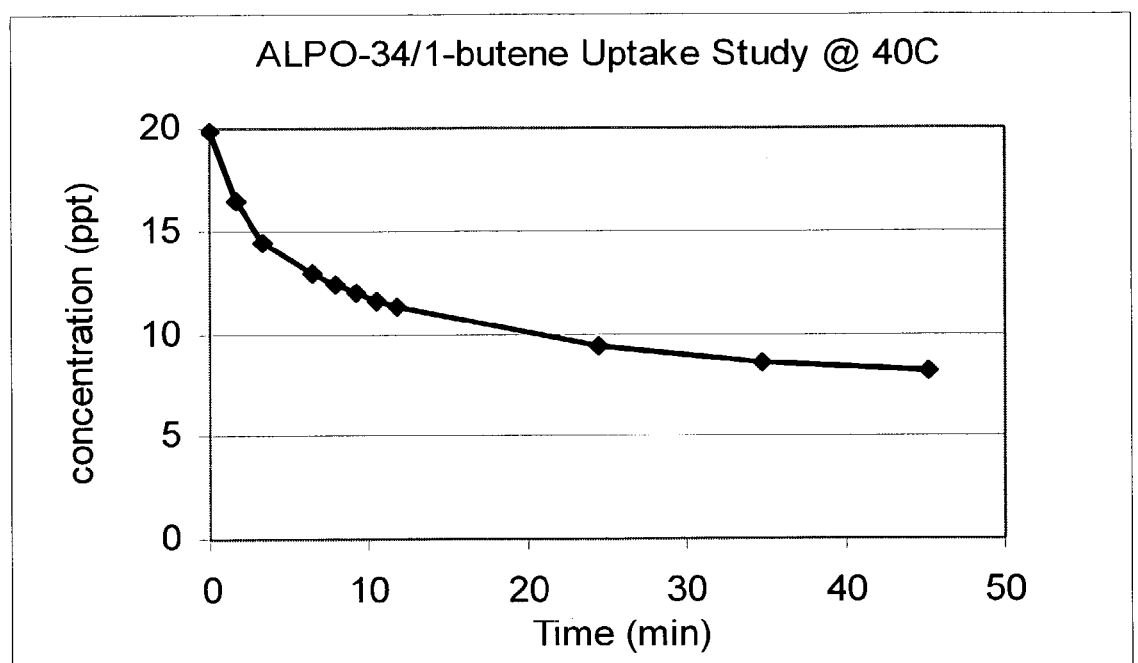
FIG. 5 shows the adsorption uptake data for 1-butene using AlPO-34.
Figure 6:
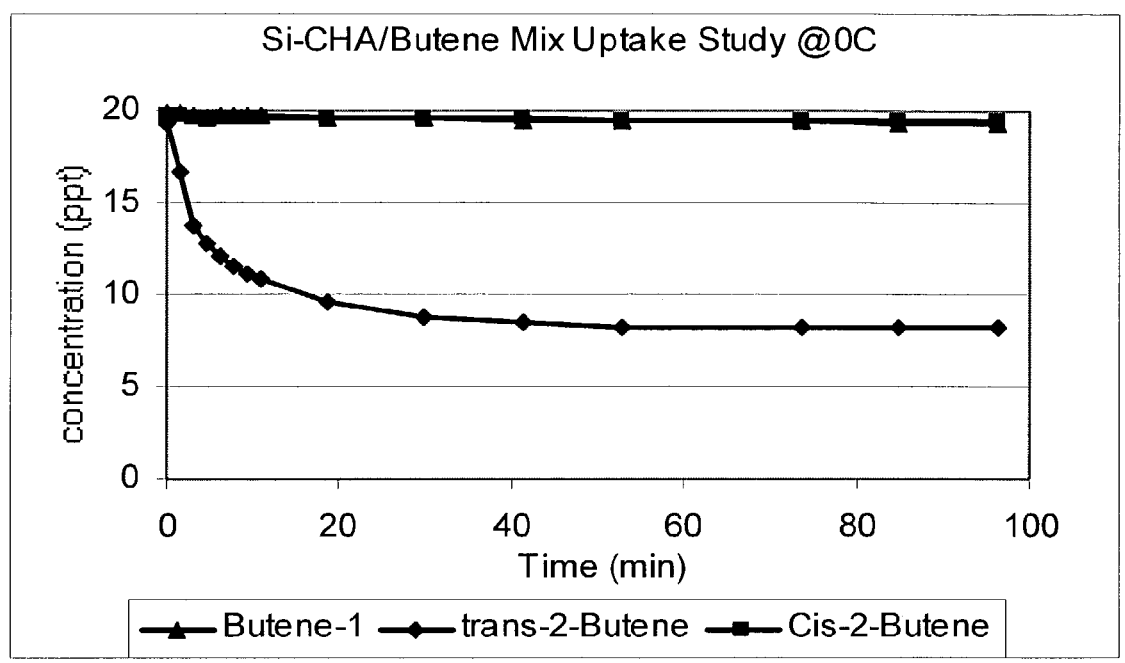
FIG. 6 shows the multi-component uptake data for a mixed butene feed using Si-CHA at 0° C. The filled triangles representing butene-1 overlap the data points for cis-2-butene in the Figure.
Figure 7:
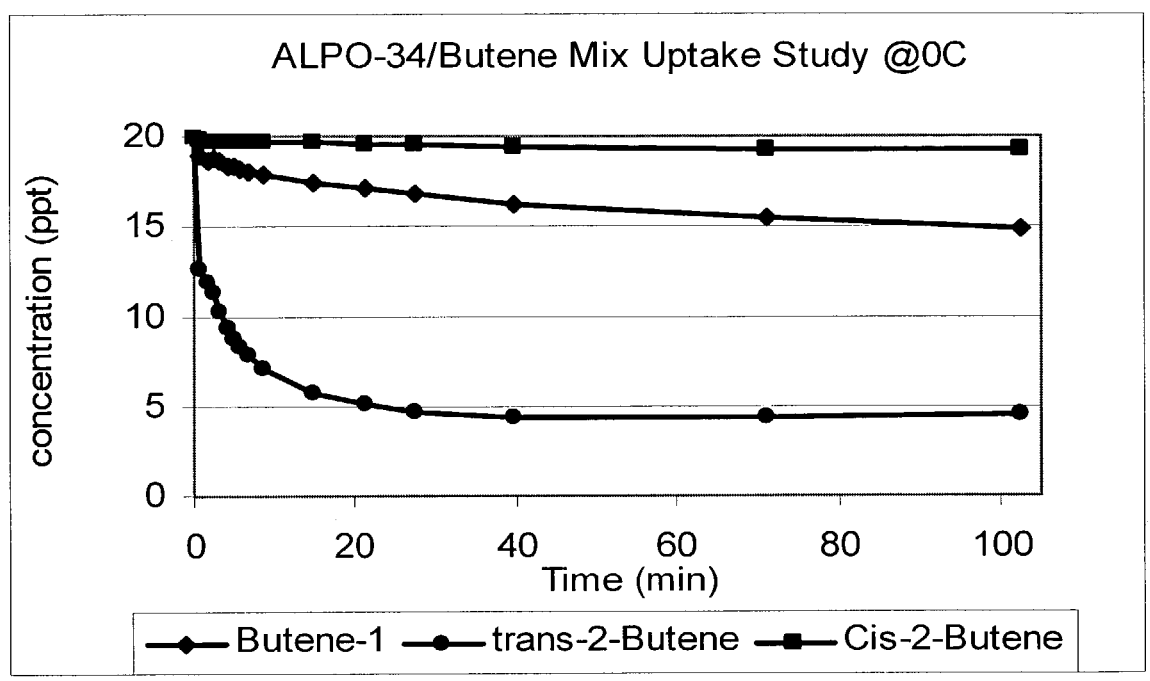
FIG. 7 shows the multi-component uptake data for a mixed butene feed using AlPO-34 at 0° C.
Figure 8:
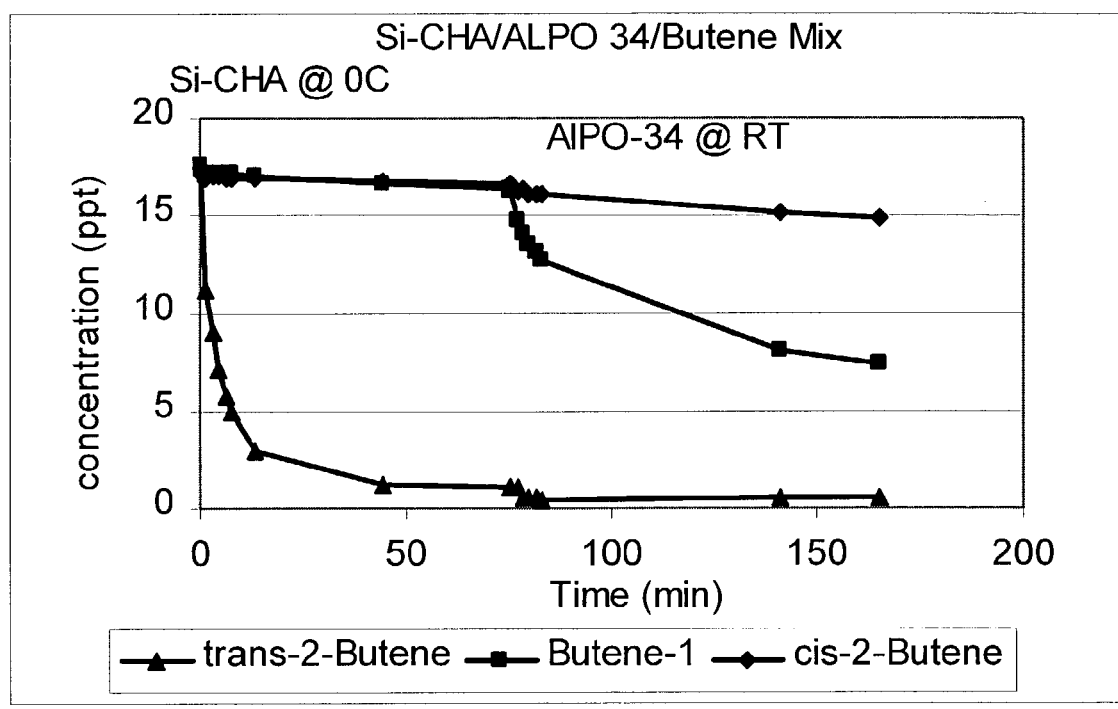
FIG. 8 shows the dual-bed in-series adsorption data for a mixed butene feed using both Si-CHA and AlPO-34.

Work by the present inventors has shown that, for the purpose of separating linear butene isomers, a more optimal control of window size, adsorption capacity, and chemical reactivity can be obtained with certain pure silica materials as well as with a class of non-acidic crystalline microporous materials containing phosphorous in the framework. For example, selected materials having the CHA or AEI structures satisfy these optimal conditions very well. Both CFIA and AEI contain cavities that are interconnected through 8-membered ring windows that form a three-dimensional pore system. The size of the windows depends on the structure type and the type of T-atoms that make up the framework. The high dimensionality of the CHA and AEI structures, in conjunction with window size control afforded by T-atom substitutions, makes them ideally suited for applications in adsorption separation processes. High dimensionality facilitates the rapid ingress and egress of molecules via diffusional transport, increases their resistance to deactivation by pore blocking (i.e., by providing multiple paths to adsorption sites), and provides large internal surface areas for adsorption. For example, pure silica CHA, having window sizes of 3.50Å×4.17Å (as determined by the Distance Least Square, DLS, method and constraining the cell size to that measured for the material), allows very rapid transport of trans-2-butene while significantly delaying 1-butene and cis-2-butene. This material, which is non-acidic and has a large capacity for adsorbing trans-2-butene, has ideal properties for a kinetic-based separation scheme in which trans-2-butene can be produced in very high purity by properly controlling the duration of the adsorption cycle. Similarly, AlPO-34, which is non-acidic and iso-structural with CHA, has DLS window apertures of 3.86Å×4.18Å. It has now been found that this seemingly small difference in window size between pure silica CHA and AlPO-34 results in a very large and unexpected change in the diffusion rates of trans-2-butene, 1-butene, and cis-2-butene. The slightly larger windows in AlPO-34 allow for rapid diffusional transport of both trans-2-butene and 1-butene, while hindering cis-2-butene. Thus, AlPO-34 has ideal properties for a kinetic-based separation scheme in which cis-2-butene can also be produced in high purity. If 1-butene is the key component to be separated from the mixture, this can be achieved, for example, by a sequential and integrated process in which the mixture containing all the olefin isomers is first contacted with a bed of pure silica CHA and then contacted with a bed containing AlPO-34. From the discussion above, it follows that such a scheme allows for the complete separation of the individual components in the mixture.

The window sizes in the phosphorus-containing materials can be further controlled by suitable T-atom substitutions that change bond lengths and bond angles while preserving the crystalline structure. Thus, for example, the complete replacement of Al by Ga in the synthesis mixture to give GaPO-34, which is iso-structural with AlPO-34, leads to another very effective material for separating 1-butene from cis-2-butene. Some of the advantages of AlPO-34 and GaPO-34 can also be found in AlPO-18 (AEI), whose structure is closely related to that of CHA and also comprises a three-dimensional interconnected channel system of 8-membered rings having DLS apertures of 3.61Å×4.47Å. Complete substitution of Al by Ga leads to GaPO-18, which is another material than can effectively separate 1-butene from cis-2-butene in a kinetic-based separation scheme.

The diffusivity of a particular sorbate in a porous crystalline material is conveniently characterized in terms of its diffusion time constant, $D/r^2$ (1/sec), wherein D is the Fickian diffusion coefficient (cm$^2$/sec) and r is the radius of the crystallites (cm) characterizing the diffusion distance. In situations where the crystals are not of uniform size and geometry, r represents a mean radius representative of their corresponding distributions. The required diffusion time constants can be derived from standard sorption kinetics measurements as described, for example, by J. Crank in "The Mathematics of Diffusion," 2nd Ed., Oxford University Press, Great Britain, 1975, incorporated by reference herein.

The present invention is for a process for selectively separating 1-butene from a $C_4$ feed stream that comprises at least 1-butene, trans-2-butene, and cis-2-butene. The first step involves passing the feed stream through a first bed of an adsorbent comprising a crystalline microporous material to form a substantially trans-2-butene-free effluent stream. The second step involves passing the substantially trans-2-butene-free effluent stream through a second bed of an adsorbent comprising a crystalline microporous material to form a substantially 1-butene-free effluent stream. The 1-butene is typically recovered by desorbing it from the second adsorbent bed. By appropriately controlling the duration of the adsorption/desorption cycles, the present invention provides the basis for a very effective and selective kinetic-based separation scheme that allows the high purity recovery of each of the linear olefins present in the original mixture.

The $C_4$ feed stream used herein can be any of the mixed hydrocarbon streams that result from catalytic cracking and steam cracking, among other processes known in the art. The conversion of methanol to olefins is another important source of these streams that would benefit by the recovery scheme proposed in the present invention. For example, feeds that may be used for the instant invention include raffinate I and raffinate II. Typical raffinate-I and raffinate-II compositions are as follows, although one skilled in the art knows that such amounts can vary depending on the source of the feed:

TABLE 1

| Component | Raffinate I (wt. %) | Raffinate II (wt. %) |
| --- | --- | --- |
| isobutane | 21.79 | 25.100 |
| n-butane | 11.94 | 17.995 |
| 1-butene | 9.07 | 20.434 |
| isobutylene | 12.65 | 1.112 |
| trans-2-butene | 14.29 | 20.381 |
| cis-2-butene | 9.73 | 12.396 |
| 1,3-butadiene | 0.00 | 0.000 |

The recovery of 1-butene in high purity is significant for its use in polymers fabrication (e.g., ethylene/butene copolymers) or as a feedstock for fine chemicals (e.g., dimerization to octenes followed by OXO processing). The present invention can also be utilized for the selective recovery of iso-butene, which is needed in the production of methyl-tertiary-butylether ("MTBE") and other chemicals or fuels. The ability to selectively recover each of the butene isomers in high purity is important in order to circumvent current technologies that rely on costly and energy-intensive distillations.

In order to effectively utilize microporous materials as adsorbents for the kinetic-based separation of linear butenes, at least three important conditions need to be simultaneously met: (1) the materials should have the appropriate window apertures such that they provide a large enough differentiation in diffusion rates for the various components in the mixture, leading to a high separation selectivity; (2) the materials should be non-acidic so as to prevent any chemical reactions of the adsorbed molecules; and (3) the materials should possess a high adsorption capacity in order to minimize the amount of adsorbent required for the process.

Preferably, the crystalline microporous materials used in the process of the invention have at least one system of channels, each defined by an 8-membered ring of tetrahedrally coordinated framework T-atoms. More preferably, the crystalline microporous materials contain a system of three interconnecting 8-membered ring channels.

It is most preferred that the first adsorbent bed has a crystalline microporous material containing framework T-atoms made of silicon and derivatives thereof, especially all-silica zeolites. In this respect, the preferred crystalline microporous materials in the first adsorbent bed are Si-CHA and ITE.

It is most preferred that the second adsorbent bed has a crystalline microporous material containing framework T-atoms made of phosphorous and derivatives thereof. Particularly preferred materials include the aluminophosphates, such as AlPO-34 and AlPO-18, and their corresponding gallophosphates, such as GaPO-34 and GaPO-18. AlPO-34 and its synthesis are described in F. Guth, Ph.D. Thesis, Mulhouse Univ., France (1989), and in H. Halvorsen, Ph.D. Thesis, Univ. of Oslo, Norway (1996), whereas AlPO-18 and its synthesis are described in U.S. Pat. Nos. 4,310,440 and 4,385,994, the entire contents of which are incorporated herein by reference. Other crystalline microporous materials with framework T-atoms made of phosphorus are galloaluminophosphates, metalloaluminophosphates, metalloaluminophosphosilicates and derivatives thereof.

In one embodiment, a $C_4$ feed stream comprising at least 1-butene, trans-2-butene and cis-2-butene is passed through a Si-CHA adsorbent bed. After a certain time period, within which the majority of the trans-2-butene is adsorbed onto the Si-CHA adsorbent, an effluent stream substantially free of trans-2-butene is formed. This effluent stream is then passed through an AlPO-34 adsorbent bed. After another period of time, within which the majority of the 1-butene is adsorbed onto the AlPO-34 adsorbent, the remaining stream contains mostly the cis-2-butene isomer. To recover the 1-butene isomer, any of the desorbing methods disclosed hereinbelow may be used to extract the 1-butene from the AlPO-34 adsorbent.

In another embodiment, an extra step can be added to the process described above whereby the adsorbed trans-2-butene isomer may be desorbed from the Si-CHA adsorbent by any of the methods disclosed herein. Then, the recovered trans-2-butene can be combined with the remaining stream from above that contains mostly cis-2-butene to form a secondary feed stream. One of skill in the art would recognize that other butene isomers and low molecular weight hydrocarbons could be present in the remaining stream and/or the secondary feed stream. The secondary feed stream is then isomerized by methods known in the art to form an equilibrium mixture comprising at least 1-butene, trans-2-butene, and cis-2-butene. This equilibrium mixture can undergo the selective separation steps disclosed above to recover 1-butene.

Adsorption equilibrium and diffusion uptake experiments confirm that Si-CHA and AlPO-34 are excellent materials for separating the various linear butene isomers of interest in the present invention. They are non-reactive, they exhibit high adsorption capacities, and they selectively transport the various isomers into the adsorbent. However, while Si-CHA and AlPO-34 appear to be excellent materials for separating 1-butene, trans-2-butene and cis-2-butene, there are many other materials that are also highly advantageous for the same purpose. In particular, phosphorus-containing crystalline microporous materials that could deliver equal or even improved performance depending on the optimization of the PSA/TSA process can be obtained upon suitable modifications in chemical composition. Thus, for example, one can envision process conditions in which shorter cycle times may be obtained at the expense of decreased separation selectivity (i.e., lower purity). A material with slightly greater window size could satisfy these conditions. Alternatively, if improvements in separation selectivity justify slightly longer cycle times, it may be advantageous to incorporate selected metals into the framework in such a manner that the effective size of the windows is slightly reduced. In general, the materials needed for specific situations can be optimized by suitable choices of the type of microporous structure, the framework atoms, and the type and charge of any non-framework balancing cations provided that any detrimental catalytic activity is avoided.

The process of the invention can be carried out in a system comprising a single adsorption bed or a plurality of adsorption beds operated either in phase or out of phase. With a system comprising a single adsorption bed or a plurality of beds operated in phase, the adsorption step must be periodically stopped to permit regeneration of the adsorbent bed(s), whereas when a plurality of adsorption beds are employed in parallel and operated out of phase, one or more beds can be in service adsorbing the desired gas component, while one or more other units can undergo regeneration to desorb and collect the adsorbed gas component. Operation of the adsorption process of the invention is cyclical. In the preferred adsorption process, cycles are repeatedly carried out in a manner such that production of the desired product gas is substantially continuous. In the preferred embodiment, therefore, the process is carried out in a system comprising a plurality of adsorption beds arranged in parallel and operated out of phase, such that at least one bed is always in the adsorption phase while another is always in the adsorbent regeneration phase.

The process of the invention may be operated as either a pressure swing adsorption (PSA) process or a temperature swing adsorption (TSA) process. In either case, the precise steps used in carrying out the separation are not critical to the invention.

In general, the basic steps in a PSA process include an adsorption vessel pressurization step, a production (adsorption) step and an adsorbent regeneration step. During the vessel pressurization step, the pressure in the adsorption vessel in which the adsorption process is carried out is raised to the desired adsorption pressure. During the production step, a gaseous $C_4$-containing feed is passed through the adsorption vessel at the desired adsorption pressure. As the feed gas passes through the adsorption vessel (e.g., in a first bed containing Si-CHA), a trans-2-butene-enriched component is adsorbed and a trans-2-butene-depleted non-adsorbed gas fraction—i.e., the effluent stream—passes out of the adsorption vessel. The bed regeneration step is carried out by reducing the pressure in the adsorption vessel so as to desorb the trans-2-butene-enriched product gas from the vessel. The same is done (e.g., in a second adsorbent bed containing AlPO-34) to adsorb 1-butene from the trans-2-butene-free effluent stream.

The temperature at which the adsorption step of the PSA process is carried out is not critical but in general will be between about −50° C. and about 250° C., or more preferably between about 0° C. and about 200° C. The upper temperature is selected so as to achieve significant loading onto the material and to avoid the possibility of any unwanted reactions, such as oligomerization and/or polymerization of the olefins. The pressures at which the adsorption and adsorbent regeneration steps are carried out are likewise a matter of choice, and in general, these steps can be carried out at any of the usual pressures employed for gas PSA processes. The pressure at which the adsorption step is carried out is determined by economics. Typically, the adsorption step is carried out at butenes partial pressures in the range of about 3 kPa to about 300 kPa, and preferably in the range of about 5 kPa to about 200 kPa. Typically, the adsorbent regeneration step is carried out at pressures in the range of about 0.1 kPa to about 10 kPa, and preferably in the range of about 0.2 kPa to about 5 kPa.

Where the process of the invention is operated as a TSA process, the production (adsorption) step is carried out at a first temperature and an adsorbent regeneration step is carried out at a second higher temperature so as to desorb the component adsorbed during the production step. In this case, the adsorption step is carried out at temperatures in the range of about −50° C. to about 200° C., preferably in the range of about 0° C. to about 150° C., while the adsorbent regeneration step is carried out at temperatures in the range of about 100° C. to about 300° C., preferably in the range of about 150° C. to about 250° C. The adsorption and regeneration steps in a TSA process are typically carried out at butenes partial pressures in the range of about 10 kPa to about 300 kPa, and preferably in the range of about 20 kPa to about 200 kPa.

The diffusional uptake of linear butene isomers on selected microporous materials were determined by measuring the composition of the butene isomers in contact with the adsorbent in a batch system using a gas chromatograph (GC). The GC was equipped with an alumina column capable of separating each of the butene isomers. The time dependence of the uptake process and its approach to equilibrium was determined by taking periodic samples of the gas. The value of the gas phase composition as a function of time included a correction for the amount of gas removed from the batch system with each sampling. The experiments were conducted in a 215 cc stainless steel recycle loop reactor in which the reactant gas mixture is repeatedly passed over a fixed bed of 90–150 mg of adsorbent such that the gas phase mixing time is significantly less than the time required to achieve equilibrium with the adsorbent. The gas was circulated by means of a positive displacement pump that delivered a flow rate of approximately 300 cc/min. A Baratron capacitance manometer (MKS, 10000 torr) was used to monitor the total gas pressure and a type K thermocouple was attached to the outside of the adsorbent bed to monitor the adsorption temperature. Si-CHA and AlPO-34 were prepared according to literature methods. See M. J. Diaz-Cabañas, et al., "Synthesis and Structure of Pure $SiO_2$ Chabazite: the $SiO_2$ Polymorph with the Lowest Framework Density," Chem. Commun., 1881 (1998); F. Guth, Ph.D. Thesis, Mulhouse Univ., France (1989); and H. Halvorsen, Ph.D. Thesis, Univ. of Oslo, Norway (1996). The adsorbents were calcined at 650° C. under flowing air for 2 hours and stored in a nitrogen drybox (<1 ppm $O_2$; <1 ppm $H_2O$).

In all the diffusional uptake experiments, the adsorbents were introduced in powder form without diluents. The adsorbent (~90–150 mg) was charged to a quartz U-tube (volume=15 cc) in a nitrogen-purged drybox (<1 ppm $O_2$ and <1 ppm $H_2O$) and held in place by utilizing quartz wool. The quartz U-tube was transported and clamped into the loop reactor and placed under vacuum. The adsorbent bed was then heated to 650° C. under flowing air for 12 hours, followed by cooling to room temperature under vacuum. The adsorbent was maintained under vacuum until it was ready to be contacted with the desired gas mixture.

The equilibrium adsorption isotherms were measured with a Quantachrom Autosorb-1 adsorption apparatus. They were determined for both Si-CHA and AlPO-34, typically at 40° C. and 60° C., for each butene isomer. Prior to contact with the butenes, the adsorbent was subjected to a thermal pre-treatment that consisted of heating the sample to 350° C. in helium and then to 550° C. in air for 2 hours. The sample was then cooled under vacuum to the desired temperature for analysis.

Adsorption experiments were conducted utilizing premixed gases (butene(s) in Ar or He) at a starting total pressure of 1500 torr. The premixed gases were introduced either as a single component (e.g., 2% 1-butene/Ar) or as multi-component mixtures [e.g., (2% 1-butene, 2% trans-2-butene, 2% cis-2-butene)/He]. Prior to contacting the adsorbent with the gas mixture, the gas manifold was monitored for the presence of air to ensure that the manifold was air-tight.

The invention will now be more particularly described with reference to the following Examples and the accompanying drawings.

EXAMPLES

Example 1

Isotherm Data of Trans-2-Butene on Si-CHA

Freshly prepared Si-CHA (24 mg) was charged in a quartz U-tube and placed into the Autosorb adsorption apparatus. The sample was evacuated and subsequently heated to 550° C. in air, followed by slow cooling under vacuum. The adsorbent was then heated to 40° C. and dosed with trans-2-butene up to specific pressures ranging from 0 to 200 torr. The results indicate that, at 40° C., Si-CHA has a very large adsorption capacity for trans-2-butene: approximately 52 ccSTP/g, which corresponds to approximately 12 wt. %. The above procedure was repeated for adsorption at 60° C.

Example 2

Isotherm Data of 1-Butene on AlPO-34

Freshly prepared AlPO-34 (56 mg) was placed in a quartz U-tube and placed into the Autosorb adsorption apparatus. The sample was evacuated and subsequently heated to 550° C. in air, followed by cooling under vacuum. The material was then heated to 40° C. and dosed with 1-butene up to specific pressures ranging from 0 to 200 torr. The results indicate that, at 40° C., AlPO-34 has a very large adsorption capacity for 1-butene: approximately 55 ccSTP/g, which corresponds to approximately 12.5 wt. %. The above procedure was repeated for adsorption at 60° C.

Example 3

Diffusional Uptake of Trans-2-Butene Utilizing Si-CHA

In a drybox, freshly prepared Si-CHA (142 mg) was charged into a quartz U-tube and then placed into the recycle loop reactor. The adsorbent bed was heated to 300° C. under vacuum for 4 hours and then allowed to cool to room temperature. The adsorbent was then isolated and the recycle loop was charged with trans-2-butene (2% in He, total pressure of 1500 torr). After cooling the system to 0° C., the mixture was continuously circulated through the adsorbent bed for a period of about 45 minutes. The concentration of trans-2-butene in the flowing stream was measured by gas chromatography.

Example 4

Diffusional Uptake of 1-Butene Utilizing Si-CHA

In a drybox, freshly prepared Si-CHA (142 mg) was charged into a quartz U-tube and then placed into the recycle loop reactor. The adsorbent bed was heated to 300° C. under vacuum for 4 hours and then allowed to cool to room temperature. The adsorbent was then isolated and the recycle loop was charged with 1-butene (2% in He, total pressure of 1500 torr). After heating the system to 40° C., the mixture was continuously circulated through the adsorbent bed for a period of about 45 minutes. The concentration of 1-butene in the flowing stream was measured by gas chromatography.

Example 5

Diffusional Uptake of 1-Butene Utilizing AlPO-34

In a drybox, freshly prepared AlPO-34 (102 mg) was charged into a quartz U-tube and then placed into the recycle loop reactor. The adsorbent was heated to 300° C. under vacuum for 4 hours and then allowed to cool to room temperature. The adsorbent was then isolated and the recycle loop was charged with 1-butene (2% in He, total pressure of 1500 torr). After heating the system to 40° C., the mixture was continuously circulated through the adsorbent bed for a period of about 45 minutes. The concentration of 1-butene in the flowing stream was measured by gas chromatography.

Example 6

Multi-Component Diffusional Uptake Experiment with Si-CHA

In the drybox, freshly prepared Si-CHA (64 mg) was charged into a quartz U-tube reactor and placed into the loop reactor. The adsorbent was heated to 300° C. under vacuum for 4 hours and then allowed to cool to room temperature. The adsorbent was isolated and the loop was charged and stirred with a mixture of trans-2-butene, cis-2-butene and 1-butene (2% of each in He, 1500 torr) and analyzed by GC to ensure that no air was present. The adsorbent was cooled to 0° C. and the reactor tube was opened. The uptake of each isomer was monitored by gas phase GC analysis. The data indicates that trans-2-butene is quickly adsorbed while both cis-2-butene and 1-butene showed little to no adsorption even after more than 1 hour of contacting with the adsorbent.

Example 7

Multi-Component Diffusional Uptake Experiment with AlPO-34

In the drybox, freshly prepared AlPO-34 (108 mg) was charged into a quartz U-tube reactor and placed into the loop reactor. The adsorbent was heated to 300° C. under vacuum for 4 hours and then allowed to cool to room temperature. The adsorbent was isolated and the loop was charged and stirred with a mixture of trans-2-butene, cis-2-butene, and 1-butene (2% of each in He, 1500 torr) and analyzed by GC to ensure that no air was present. The adsorbent was cooled to 0° C. and the reactor tube was opened. The uptake of each isomer was monitored by gas phase GC analysis. The data reveals that trans-2-butene is quickly adsorbed, 1-butene is also adsorbed but at a slower rate, and cis-2-butene showed little to no adsorption even after more than 1 hour of contacting with the adsorbent.

Example 8

Dual-Bed Adsorption Process

In the drybox, freshly prepared AlPO-34 (108 mg) and Si-CHA (142 mg) were charged into separate quartz U-tube reactors and both were connected in series to the recycle loop reactor. Both of the adsorbents were heated to 300° C. under vacuum for 4 hours and then allowed to cool to room temperature. The adsorbents were isolated and the loop was charged with a mixture of trans-2-butene, cis-2-butene and 1-butene (2% of each in He, total pressure of 1500 torr) and analyzed by gas chromatography to ensure that no air was present. The Si-CHA adsorbent was cooled to 0° C., while the AlPO-34 adsorbent was maintained at room temperature. With the AlPO-34 adsorbent bed isolated, the Si-CHA adsorbent bed was exposed to the butenes mixture. The uptake of each isomer was monitored by gas phase GC analysis. Whereas trans-2-butene was quickly adsorbed into the material, cis-2-butene and 1-butene showed little to no adsorption even after 1 hour on stream. After a period of about 80 minutes, in which trans-2-butene was approaching equilibrium with the adsorbent, the Si-CHA adsorbent bed was isolated and the AlPO-34 adsorbent bed was exposed to the gas mixture. GC analysis indicated that 1-butene was quickly adsorbed, while only a small amount of cis-2-butene was adsorbed even after more than 1 hour on stream.

The invention having been thus described, it will be apparent that the same may be varied in many ways without departing from the spirit and scope of the invention, as defined by the following claims.

What is claimed is:

1. A process for selectively separating 1-butene from a $C_4$ feed stream comprising at least 1-butene, trans-2-butene and cis-2-butene, the process comprising the steps of:
    (a) passing the feed stream through a first bed of an adsorbent comprising a crystalline microporous material to form a substantially trans-2-butene-free effluent stream; and
    (b) passing the effluent stream through a second bed of an adsorbent comprising a crystalline microporous material to form a substantially 1-butene-free effluent stream,
   whereby the 1-butene is separated from the feed stream, wherein the crystalline microporous materials of steps (a) and (b) comprise different cation-free non-acidic crystalline microporous materials, wherein the window size of the cation-free non-acidic crystalline microporous material of step (b) is larger than the window size of the cation-free non-acidic crystalline microporous material of step (a).

2. The process of claim 1 wherein the crystalline microporous materials of steps (a) and (b) comprise crystalline microporous materials having at least one system of channels, wherein each system is defined by an 8-membered ring of tetrahedrally coordinated framework T-atoms.

3. The process of claim 2 wherein the crystalline microporous materials of steps (a) and (b) comprise crystalline microporous materials having a system of three interconnecting 8-membered ring channels.

4. The process of claim 2 wherein the framework T-atoms of step (a) comprise silicon and derivatives thereof.

5. The process of claim 4 wherein the crystalline microporous material of step (a) comprises Si-CHA.

6. The process of claim 4 wherein the crystalline microporous material of step (a) comprises ITE.

7. The process of claim 4 wherein the framework T-atoms of step (b) comprise phosphorus and derivatives thereof.

8. The process of claim 7 wherein the crystalline microporous material of step (b) is selected from the group consisting of aluminophosphates, gallophosphates, galloaluminophosphates, metalloaluminophosphates, metalloaluminophosphosilicates and derivatives thereof.

9. The process of claim 7 wherein the crystalline microporous material of step (b) is selected front the group consisting of AlPO-34, AlPO-18, GaPO-34 and GaPO-18.

10. The process of claim 1 wherein steps (a) and (b) are performed under kinetic-based adsorption conditions.

11. The process of claim 10 wherein steps (a) and (b) are performed under pressure swing adsorption conditions.

12. The process of claim 10 wherein steps (a) and (b) are performed under temperature swing adsorption conditions.

13. The process of claim 10 wherein steps (a) and (b) are performed under a combination of pressure and temperature swing adsorption conditions.

14. The process of claim 1 wherein each of steps (a) and (b) are performed within prescribed adsorption times.

15. The process of claim 14 wherein the adsorption times of steps (a) and (b) comprise durations maximizing the uptake of trans-2-butene and J-butene, respectively.

16. The process of claim 1 further comprising the step of desorbing the 1-butene from the second adsorbent bed, whereby the 1-butene is recovered from the feed stream.

17. The process of claim 1 further comprising the steps of:
(c) desorbing the trans2-butene from the first adsorbent bed;
(d) collecting the effluent stream from step (b) above and the desorbed trans-2-butene from step (c) above to form a secondary feed stream;
(e) isomerizing the secondary feed stream to form an equilibrium mixture of at least 1-butene, trans-2-butene and cis-2-butene; and
(f) repeating the steps of claim 1.

* * * * *